US011028034B2

(12) United States Patent
Backes et al.

(10) Patent No.: US 11,028,034 B2
(45) Date of Patent: Jun. 8, 2021

(54) METHOD FOR PRODUCING ROTUNDONE-CONTAINING MIXTURES

(71) Applicant: SYMRISE AG, Holzminden (DE)

(72) Inventors: Michael Backes, Holzminden (DE); Tobias Vössing, Beverungen (DE); Nadine Heinemeier, Bevern (DE); Lars Meier, Derental (DE); Dietmar Schatkowski, Einbeck (DE); Willi Krieger, Brakel (DE); Katharina Reichelt, Holzminden (DE); Susanne Otte-Hölscher, Halle (DE)

(73) Assignee: SYMRISE AG, Holzminden (DE)

( * ) Notice: Subject to any disclaimer, the term of this patent is extended or adjusted under 35 U.S.C. 154(b) by 86 days.

(21) Appl. No.: 16/488,408

(22) PCT Filed: Feb. 27, 2017

(86) PCT No.: PCT/EP2017/054524
§ 371 (c)(1),
(2) Date: Aug. 23, 2019

(87) PCT Pub. No.: WO2018/153499
PCT Pub. Date: Aug. 30, 2018

(65) Prior Publication Data
US 2020/0247740 A1 Aug. 6, 2020

(51) Int. Cl.
C07C 45/34 (2006.01)
C07C 49/00 (2006.01)
A23L 27/20 (2016.01)
A23L 33/105 (2016.01)
C07C 49/653 (2006.01)

(52) U.S. Cl.
CPC ............ C07C 45/34 (2013.01); A23L 27/203 (2016.08); A23L 33/105 (2016.08); C07C 49/653 (2013.01)

(58) Field of Classification Search
CPC ..... C07C 45/34; C07C 49/653; A23L 27/203; A23L 33/105
See application file for complete search history.

(56) References Cited

FOREIGN PATENT DOCUMENTS

| CH | 263793 A | 9/1949 |
|----|----------|--------|
| JP | 2013534927 A | 9/2013 |
| JP | 2016198026 A | 12/2016 |
| WO | 2012001018 A1 | 1/2012 |

OTHER PUBLICATIONS

European Office Action dated Oct. 16, 2020 for corresponding European Application No. EP 17708202.1.
Loic Tissandie et al., "Revisiting the Chemistry of Guaiacwood Oil: Identification and Formation Pathways of 5,11- and 10,11-Epoxyguaianes", Journal of Natural Products, vol. 80, Nr. 2, 2017, pp. 526-537 XP055737548.
Japanese Office Action dated Aug. 24, 2020 for corresponding Japanese Application No. 2019-546862.
An-Cheng Huang et al., "Production of the Pepper Aroma Compound, (−)-Rotundone, by Aerial Oxidation of β-Guaiene", Journal of Agricultural and Food Chemistry, vol. 62, No. 44, 2014, pp. 10809-10815.
International Search Report and Written Opinion dated May 11, 2017, for corresponding PCT Application No. PCT/EP2017/054524.
Wood, Claudia et al., "From Wine to Pepper: Rotundone, an Obscure Sesquiterpene, Is a Potent Spicy Aroma Compound", Journal of Agricultural and Food Chemistry, vol. 56, No. 10, 2008, pp. 3738-3744 XP055366765.

*Primary Examiner* — Sikarl A Witherspoon
(74) *Attorney, Agent, or Firm* — Polsinelli PC

(57) ABSTRACT

The present invention relates to, according to a primary aspect, a method for manufacturing a mixture comprising rotundone. A further aspect of the present invention relates to mixtures containing rotundone as well as their use for generating, imparting or modifying, preferably enhancing, one or several taste and/or olfactory impressions. Moreover, the invention relates to a pharmaceutical preparation for nutrition, for oral care or for pleasure or a cosmetic pharmaceutical preparation or a pharmaceutical preparation intended for oral consumption or an intermediate good for manufacturing a pharmaceutical preparation for nutrition, for oral care or for pleasure or a cosmetic pharmaceutical preparation or a pharmaceutical preparation intended for oral consumption comprising a mixture according to the invention and furthermore to a method for manufacturing said preparation or intermediate good.

20 Claims, No Drawings

METHOD FOR PRODUCING ROTUNDONE-CONTAINING MIXTURES

CROSS-REFERENCE TO RELATED APPLICATIONS

This application is a national stage application (under 35 U.S.C. § 371) of PCT/EP2017/054524, filed Feb. 27, 2017, which is incorporated herein by reference in its entirety.

The present invention relates to, according to a primary aspect, a method for manufacturing a mixture comprising rotundone. A further aspect of the present invention relates to mixtures containing rotundone as well as their use for generating, imparting or modifying, preferably enhancing, one or several taste and/or olfactory impressions. Moreover, the invention relates to a pharmaceutical preparation for nutrition, for oral care or for pleasure or a cosmetic pharmaceutical preparation or a pharmaceutical preparation intended for oral consumption or an intermediate good for manufacturing a pharmaceutical preparation for nutrition, for oral care or for pleasure or a cosmetic pharmaceutical preparation or a pharmaceutical preparation intended for oral consumption comprising a mixture according to the invention and furthermore to a method for manufacturing said preparation or intermediate good.

Rotundone ((3S,5R,8S)-3,4,5,6,7,8-hexahydro-3,8-dimethyl-5-(1-methylethenyl)-1 (2H)-azulenone, CAS #18374-76-0) was detected in nature in different wines as well as black pepper and various herbs (*J. Agric. Food Chem.* 2008, 56, 3738-3744). Furthermore, rotundone is described as the compound with the highest impact in cypriole oil (*J. Agric. Food. Chem.* 2016, 64, 4566-4573). Rotundone is also present in incense (*J. Nat. Prod.* 2016, 79, 1160-1164).

In WO 2015 181 257, perfume compositions with special spatiotemporal profiles are described, which can also contain, amongst many others, rotundone.

Moreover, rotundone was identified in various fruits (explicitly mentioned: grapefruit, orange, apple and mango) and the positive effect of rotundone in fruit aromas was sensorially described, wherein herein rather the woody notes are paramount (poster at the Wartburg Symposium 2016). The enhancement of fruit aroma was recently described by the same group in the published patent application JP 2016 198 026.

The manufacturing of rotundone from guaiol (extracted from guaiac wood oil) via the corresponding guaiene is also described in literature. In the described synthesis, however, the pure substance is used and organometallic reagents are used (*J. Agric. Food Chem.* 2008, 56, 3738-3744 and *Indian Journal of Chemistry, Section B: Organic Chemistry Including Medicinal Chemistry* 1983, 22B, 1060).

The document WO 2011/106166 A1 also describes the manufacturing of rotundone from guaiene through oxidation using a metal-based catalyst.

EP 2 588 436 B1 discloses the manufacturing of rotundone directly from guaiene using laccase. Thereby, a new mixture of rotundone and the corresponding rotundol as well as further byproducts forms.

Also described is the autoxidation of guaiene in organic solvents or on filter paper (*J. Agric. Food Chem.* 2014, 62, 10809-10815). Moreover, studies about the mechanism of said autoxidation are known (*J. Nat. Prod.* 2015, 78, 131-145; *J. Agric. Food Chem.* 2015, 63, 1932-1938).

Recently, an improved strategy for the synthesis of rotundone with the aid of electrochemistry was presented (*Nature* 2016, 533, 77-81). However, to date no synthesis strategy is disclosed in the literature, with which rotundone can be prepared on an industrially relevant scale and in acceptable purity.

The aroma industry is always searching for new raw materials, which allow the formulation of authentic, natural aromas. These characteristics are attributed to rotundone, however, an industrially feasible manufacturing method of this raw material was lacking until now (especially within the framework of the relevant EU legislation).

Surprisingly, it was found in the course of the studies underlying the present invention, that by treatment of wood oils, extracts and/or natural resins containing guaiol and bulnesol, especially of guaiac wood oil, with organic acids and air (if necessary under addition of a solvent), a mixture containing further components besides rotundone is obtained, which when used in aromas advantageously enhance their authenticity and impact. The mixtures according to the invention can advantageously be used as natural aromas according to the regulation (EG) number 1334/2008 of the European parliament and the council regarding aromas and certain food ingredients with aroma characteristics for use in and on food.

According to a primary aspect, the present invention therefore relates to a method for manufacturing a mixture comprising rotundone, comprising or consisting of following steps:

a) Reaction of wood oil(s), extract(s) and/or natural resin(s), preferably of guaiac wood oil, containing guaiol and bulnesol, preferably containing 15 to 45% by weight guaiol and 25 to 55% by weight bulnesol, more preferably containing 20 to 35% by weight guaiol and 30 to 45% by weight bulnesol, with one or several organic acid(s), or providing wood oil(s), extract(s) and/or natural resin(s) containing guaiene and bulnesene, organic

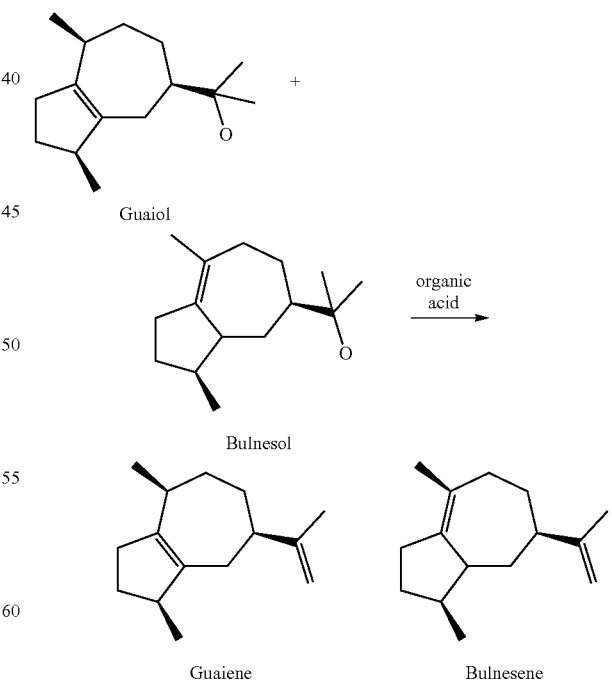

b) Separating the guaiene containing fraction from the mixture obtained or provided in step a), preferably by distillation, c) Oxidation of the separated guaiene containing fraction of step b), preferably with ambient air and/or pure oxygen as oxidizing agent,

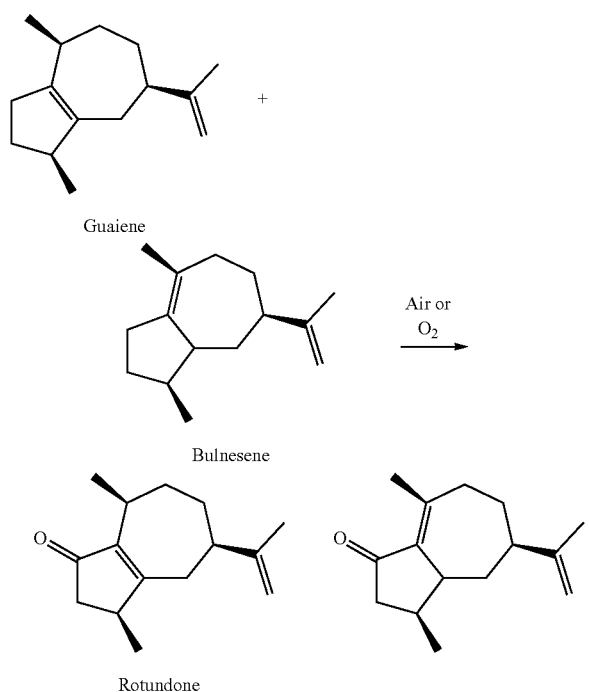

d) optionally: Heating of the oxidized mixture obtained in step c), preferably heating over a period of time of 1 to 3 hours and/or at 110 to 150° C., preferably at 115 to 125° C., e) Separating the rotundone containing fraction from the mixture obtained in step c) or d), if present, preferably by distillation, to obtain the rotundone containing mixture.

The wood oil(s) used in step a) of the method according to the invention is/are preferably guaiac wood oil, preferably obtained from wood of the tree species *Bulnesia sarmientoi*, and/or wood oil obtained from the species *Callitris glaucophylla*. The natural resin(s) used in step a) of the method according to the invention is/are preferably guaiac resin, preferably obtained from the tree species *Bulnesia sarmientoi, Guaiacum officinale* and/or *Guaiacum sanctum*. Moreover, it is possible to use extracts of certain plant species, preferably of ferula species, as sources for guaiol and bulnesol or of guaiene and bulnesene within the framework of the present invention.

Guaiac wood oil containing guaiol and bulnesol is preferably extracted by steam distillation from bark or wood of the tree species *Bulnesia sarmientoi*. Furthermore, other guaiac species, for example *Guaiacum officinale* and/or *Guaiacum sanctum* can be used as starting material.

According to a preferred embodiment of the method according to the invention, wood oil(s), extract(s) and/or natural resin(s) containing guaiene and bulnesene can be used as staring materials of the method. In this case, the reaction of guaiol and bulnesol is omitted (as described above).

The pure oxygen used in step c) of the method according to the invention, if present, preferably is oxygen with a purity of ≥99.9% by volume, more preferably of ≥99.99% by volume, especially preferably of ≥99.998% by volume. Preferably, ambient air (i.e. the oxygen contained in the ambient air) is used as oxidizing agent in step c) of the method according to the invention. This allows an especially cheap manufacturing method of mixtures containing rotundone, especially on industrial scale.

The method according to the invention is especially advantageous, because its products (i.e. the mixtures according to the invention comprising rotundone), precursors as well as all further components used in the method are usable without any concerns from a food technological and legal point of view. Advantageously, the method relies on the use of renewable raw materials and does not use any organometallic reagents. Moreover, the method according to the invention does not require any complex or unusual process steps or procedures, so that it can be used in common production facilities without problems and on industrial scale. The mixture comprising rotundone obtained by the method according to the invention is especially stable and therefore broadly usable in aromas and food and is compatible with various other components.

According to a preferred embodiment of the method according to invention the organic acid(s) used in step a) is or are selected from the group consisting of citric acid, malic acid, tartaric acid and oxalic acid, preferably the organic acid used in step a) is tartaric acid.

According to one embodiment, the organic acid can be added completely at the beginning of the reaction in step a) of the method. However, a repeated addition of smaller amounts has been shown to be preferred. Therefore, preferably, half of the acid is added at the beginning of the reaction in step a) of the method und after half of the reaction time of the reaction in step a) the second half of the acid is added.

According to a further preferred embodiment of the method according to the invention, in step a) the weight ratio of wood oil(s), extract(s) and/or natural resin(s) containing guaiol and bulnesol to organic acid or to organic acids is between 50:1 and 3:1, preferably between 20:1 and 2:1, especially preferably between 12:1 and 8:1.

According to another preferred embodiment of the method according to the invention, the reaction in step a) takes place in the presence of a co-solvent or several co-solvents, preferably in the presence of a polyethylene glycol or several polyethylene glycols, especially preferably in the presence of PEG 600, and preferably the weight ratio of wood oil(s), extract(s) and/or natural resin(s) containing guaiol and bulnesol to the one or several co-solvent(s) is 4:1 to 1:2.

The addition of one co-solvent or several co-solvents to the mixture before or during the reaction in step a) of the method is especially advantageous, as the presence of one co-solvent or several co-solvents ensures the stirrability of the reaction.

According to another preferred embodiment of the method according to the invention, the reaction temperature of the reaction in step a) is between 160 and 260° C., preferably between 180 and 220° C., and/or the reaction time of the reaction in step a) is between 1 and 20 h, preferably between 5 and 15 h, and/or the reaction in step a) is conducted at normal pressure or at negative pressure, preferably at 400 to 900 mbar, especially preferably at 500 to 700 mbar.

Within the framework of the present invention, normal pressure means atmospheric pressure without use of a vacuum. This is usually circa 1,013.25 hPa or 1.01325 bar at sea level and accordingly less at higher levels.

The reaction or dehydratisation reaction taking place in step a) of the method according to the invention is preferably conducted at negative pressure as defined above, to improve or ease the removal of the generated reaction water.

According to another preferred embodiment of the method according to the invention, the separation of the guaiene containing fraction from the mixture obtained in step a) takes place in step b) by distillation, preferably at negative pressure, preferably at 1.0 to 20.0 mbar and a sump temperature of 90 to 175° C., especially preferably at 2.0 to 10.0 mbar and a sump temperature of 105 to 160° C., more preferably at 4.0 mbar and a sump temperature of 130° C.

Preferably, the proportion of guaiene in the guaiene containing fraction obtained in step b) is 18% by weight or more.

According to another preferred embodiment of the method according to the invention, the oxidation of the guaiene containing fraction of step b) takes place in step c) with ambient air and/or pure oxygen as oxidizing agent and/or at a temperature of 60 to 150° C., preferably at 80 to 130° C., especially preferably at 90 to 110° C., and/or with a gas amount of oxidizing agent from ≥10 to ≤1000 l/h, preferably from ≥30 to ≤500 l/h, especially preferably from ≥40 to ≤100 l/h, per kg of precursor and/or over a period of time of 10 to 60 h, preferably of 15 to 30 h.

Within the framework of this preferred embodiment, the term precursor refers to the guaiene containing fraction obtained in step b) of the method according to invention.

The use of the gas amounts of the oxidizing agent in step c) of the method as defined above is especially advantageous, because the yield is often too small at small air amounts and higher air amounts lead to the formation of byproducts or degradation of the forming desired products.

Preferably, the oxidation in step c) of the method according to the invention is conducted until a noticeable decline of the reaction speed begins. The decline of reaction speed is preferably determined by sampling (from the reaction flask) and analysis or by measuring of the oxygen consumption in the exhaust air during the oxidation reaction. Preferably, the weight ratio of the non-reacted guaiene to rotundone after finishing the oxidation reaction in step c) is between 12:1 and 3:1 and the amount of rotundone in this mixture lies at >2000 ppm, especially preferably at >3500 ppm, ideally at >6000 ppm. According to another preferred embodiment of the method according to the invention, the peroxide number of the mixture obtained in step c) or d), if present, is <30 meq O/kg, preferably <20 meq O/kg.

According to a preferred embodiment, step d) is present in the method according to the invention, to advantageously destroy peroxides that possibly formed. When selecting the especially suitable conditions in step d) of the method as defined above, the content of rotundone in the mixtures is more or less retained. At higher temperatures, the degradation of the peroxides in step d) is faster, but the content of rotundone decreases significantly.

The obtained values of the rotundone content in mixture after step c) or after step d), if present, of the method according to the invention were determined in a semiquantitative way (against 2-nonanol and/or tridecane as internal standard), preferably with the aid of gas chromatographic methods. These values can vary depending on the method and selected standard.

According to another preferred embodiment of the method according to the invention, one or more entrainer(s) selected from the group consisting of triacetin and triethylcitrate in a weight ratio of mixture obtained in step c) or d), if present, to entrainer(s) of 4:1 to 1:4, preferably of 3:1 to 1:1, is or are added to the mixture in step e) before and/or during distillation, and/or one or more co-solvent(s) selected from the group consisting of polyethylene glycols and palatinol Z (CAS #68515-9-1), preferably PEG 400 and/or PEG 600, is or are added in a weight ratio of mixture obtained in step c) or d), if present, to co-solvent(s) of 10:1 to 1:5, preferably of 5:1 to 1:1.

The addition of one or more entrainer(s) and/or co-solvents before and/or during distillation in step e) of the method according to the invention is especially advantageous, because the entrainer(s) lead(s) to an easier and more efficient distillation or separation of the rotundone containing mixture and the addition of co-solvent(s) ensures the stirrability of the distillation sump. Preferably, an entrainer is used, which is approved as solvent for aromas.

According to another preferred embodiment of the method according to the invention, the separation of the rotundone containing fraction from the mixture obtained in step c) or d), if present, takes place in step e) by distillation, preferably at negative pressure, preferably at 3 to 5 mbar.

Preferably the rotundone containing fraction obtained in step c) or d), if present, is separated during distillation in step e) from the non-volatile polymeric components. Especially preferably a fraction with low boiling components (head temperature between 95° C. and 105° C. at 3-5 mbar), which contains no or low amounts of rotundone, is separated before. The distillation is finished when a head temperature of 130° C. to 160° C. at 3-5 mbar is reached.

Preferably, the distillate obtained in step e) is standardized by addition of further carrier substances (preferably e.g. of entrainer, preferably triethylcitrate, added before and/or during the distillation in step e)), such that in step e) a mixture is obtained containing 0.25 to 2.5% by weight, more preferably 0.50 to 1.50% by weight, rotundone, which then can be directly incorporated into aromas.

According to another embodiment, the rotundone containing mixture obtained in step e) of the method according to the invention can be again (precise-)distilled, preferably such that a mixture with a rotundone content of 3 to 15% by weight, preferably of 5 to 10% by weight, is obtained, wherein the weight ratio of rotundone to triethylcitrate, if present, preferably is between 1:3 and 1:10 in the mixture obtained after the further distillation.

The values obtained for the content of rotundone in the rotundone containing fraction obtained in step e) of the method according to the invention were determined in a semiquantitative way (against 2-nonanol or tridecane as internal standard). These values can vary depending on the method and selected standard. For the disclosure, a correction factor for triethylcitrate of 2.555 was used for the measurements against tridecane as internal standard.

The rotundone containing mixture obtained in step e) of the method according to the invention, preferably containing 0.25 to 2.5% by weight, especially preferably containing 0.50 to 1.50% by weight, rotundone, is preferably used in a concentration of 0.1 ppm to 5000 ppm, more preferably of 0.5 ppm to 500 ppm, especially preferably of 1 ppm to 200 ppm in flavouring and/or odorous substance mixtures, and/or preferably in a concentration of the rotundone containing mixture in the finished (where appropriate, the flavouring and/or odorous substance mixture containing) product (intermediate good or preparation) of preferably 0.0001 ppm to 10.0 ppm, more preferably of 0.0001 to 1.0 ppm, especially preferably of 0.0005 ppm to 0.5 ppm, particularly preferably of 0.001 ppm to 0.25 ppm.

A mixture according to the invention or a flavouring and/or odorous substance mixture containing the rotundone containing mixture obtained in step e) of the method according to the invention can be transferred prior to the following use in intermediate goods or preparations, especially those as described herein, into a desired formulation (e.g. through spray drying, preferably Evogran®).

Such a (preferably spray-dried) mixture preferably comprises besides the rotundone containing mixture obtained in step e) of the method according to the invention further odorous substance and/or flavouring compounds as well as one or several carrier(s) suitable for consumption.

Advantageous carriers in this preferred (preferably spray-dried) formulation according to the invention are silicon oxide (silica, silica gel), carbohydrates and/or carbohydrate polymers (polysaccharides), cyclodextrines, starches, degraded starches (starch hydrolysates), chemically or physically modified starches, modified celluloses, gum arabic, ghatti gum, traganth, karaya, carrageenan, guar gum, locust bean gum, alginates, pectin, inulin or xanthan gum. Preferred starch hydrolysates are maltodextrins and dextrins.

Preferred carriers are silicon oxide, gum arabic and maltodextrins, wherein here maltodextrins with DE-values in a range of 5 to 20 are preferred. It is irrelevant, which plant initially delivered the starch for manufacturing of the starch hydrolysates. Suitable and easily available are corn based starches as well as starches from tapioca, rice, wheat or potato. The carriers can also work as flowing aids herein, such as for example silicon dioxide.

The formulations according to the invention, which contain the rotundone containing mixtures obtained in step e) of the method according to the invention, as well as also comprise one or several solid carriers, can for example be processed via mechanical mixing, wherein a granulation of the particles can happen simultaneously, or can be manufactured via spray-drying. Preferred are formulations according to the invention, which comprise solid carriers und are manufactured via spray-drying; with regard to the spray-drying, it is referred to U.S. Pat. Nos. 3,159,585, 3,971,852, 4,532,145 or 5,124,162.

Preferred formulations according to the invention comprising carriers, which were manufactured via spray-drying, preferably have an average particle size in a range of 30-300 µm and a remaining moisture less than or equal 5% by weight.

Another aspect of the present invention relates to a rotundone containing mixture, (a) comprising or consisting of rotundone, bulnesene, guaiene, guaiol and bulnesol as well as optionally triethylcitrate and/or triacetin, and/or (b) producible according to a method according to the invention as defined above.

What has been said above in terms of the method according to the invention applies accordingly to the rotundone containing mixture according to the invention, its manufacturing method and preferred embodiments.

Preferred is a rotundone containing mixture according to the invention containing triethylcitrate as well as all of the compounds rotundone, bulnesene, guaiene, bulnesol and guaiol in a weight ratio of 1:1 to 30:1, more preferably of 2:1 to 25:1, especially preferably of 5:1 to 20:1. Preferably, the weight ratio of rotundone to the total amount of bulnesene and guaiene in the rotundone containing mixture according to the invention is 20:1 to 1:40, more preferably 5:1 to 1:20, especially preferably 2:1 to 1:12. Preferably, in the rotundone containing mixture according to the invention, the weight ratio of rotundone to the total amount of bulnesol and guaiol is furthermore 25:1 to 1:15, more preferably 10:1 to 1:10, especially preferably 5:1 to 1:5.

Another aspect of the present invention relates to the use of a mixture according to the invention as defined above for generating, imparting or modifying, preferably enhancing, one or several taste and/or olfactory impression(s), preferably selected from the group consisting of citrus, fruit, mint, nutmeg, pepper, spice, herbs, coffee, chocolate, nut, nut nougat impressions, stored liquors (e.g. whiskey, rum, brandy impressions), wine and savory impressions.

According to a preferred embodiment, the mixture according to the invention as defined above is used to give other flavouring compounds a more complex, natural (and, if applicable, enhanced) taste impression.

Another aspect of the present invention relates to a pharmaceutical preparation for nutrition, for oral care or for pleasure or a cosmetic pharmaceutical preparation or a pharmaceutical preparation intended for oral consumption or intermediate good for manufacturing a pharmaceutical preparation for nutrition, for oral care or for pleasure or a cosmetic pharmaceutical preparation or a pharmaceutical preparation intended for oral consumption, comprising a rotundone containing mixture according to the invention as defined above.

Preparations for nutrition or for pleasure in the sense of the present invention are e.g. bakery products (e.g. bread, dry cookies, cakes, other pastry), sweets (e.g. chocolate, chocolate bar products, other bar products, fruit gum, hard and soft caramel, chewing gum), alcoholic and non-alcoholic beverages (e.g. coffee, tea, wine, wine containing beverages, beer, beer containing beverages, liquors, schnapps, brandy, fruit containing lemonades, isotonic beverages, soft drinks, nectars, fruit and vegetable juices, fruit or vegetable juice preparations), instant beverages (e.g. instant cocoa beverages, instant tea beverages, instant coffee beverages), meat products (e.g. ham, fresh or raw sausage preparations, seasoned or marinated fresh or salt meat products), eggs or egg products (dry egg, egg white, egg yolk), cereal products (e.g. breakfast cereals, muesli bars, precooked instant rice products), dairy products (e.g. milk drinks, milk ice cream, yoghurt, kefir, fresh cheese, soft cheese, hard cheese, dry milk powder, whey, butter, buttermilk, partially or completely hydrolysed milk protein containing products), products from soy protein or other soy bean fractions (e.g. soy milk and products manufactured thereof, soy lecithin containing preparations, fermented products such as tofu or tempeh or products manufactured thereof, soy sauces), fruit preparations (e.g. jams, fruit ice cream, fruit sauces, fruit fillings), vegetable preparations (e.g. ketchup, sauces, dried vegetables, frozen vegetables, precooked vegetables, vegetables marinated in vinegar, boiled down vegetables), snacks (e.g. baked or fried potato crisps or potato dough products, bread dough products, corn- or peanut-based extrudates), fat- and oil-based products or emulsions thereof (e.g. mayonnaise, remoulade, dressings, seasonings), other instant meals and soups (e.g. dry soups, instant soups, precooked soups), spices, spice mixtures as well as seasonings, which are applied in the snack area. The preparations according to the invention can also be present in form of capsules, tablets (non-coated as well as coated tablets, e.g. with enteric coating), dragées, granulates, pellets, solid mixtures, dispersions in liquid phases, as emulsions, as powders, as solutions, as pastes or as other swallowable or chewable preparations as dietary supplements.

Pharmaceutical preparations determined for oral uptake according to the present invention are preparations, which e.g. are present in the form of capsules, tablets (non-coated as well as coated tablets, e.g. with enteric coating), dragées, granulates, pellets, solid mixtures, dispersions in liquid phases, as emulsions, as powders, as solutions, as pastes or as other swallowable or chewable preparations and are used as prescription, pharmacy-only or other pharmaceuticals or as dietary supplements.

The preparations for oral care according to the present invention are particularly mouth- and/or tooth care products such as tooth pastes, tooth gels, tooth powders, mouthwashes, chewing gums and other oral care products.

Cosmetic preparations in the framework of the present invention are e.g. cosmetic preparations for application in the body or head area such as soaps, other cleansing or care products for the face area or the body, face creams, face lotions or face ointments, sun protection products, beard cleaning or care products, shaving foams, shaving soaps or shaving gels, lipsticks or other lip cosmetics or lip care products.

Preferred amounts of rotundone contained in intermediate goods and preparations according to the invention result from the statements further above.

In an intermediate good or preparation according to the invention, usual active substances, raw materials, excipients and additives for pharmaceutical preparations for nutrition, for oral care or for pleasure or oral pharmaceutical preparations (i.e. pharmaceutical preparations determined for oral use) or cosmetic preparations in amounts of 0.9 to 99.999999% by weight, preferably of 10 to 80% by weight, relating to the total weight of the intermediate good or preparation, can be contained. In particular, an intermediate good or preparation according to the invention can contain water in an amount of up to 99.999999% by weight, preferably of 5 to 80% by weight, relating to the total weight of the intermediate good or preparation.

As further components of preparations or intermediate goods for nutrition or pleasure according to the invention usual raw materials, excipients and additives for food or luxury food in a preparation according to the invention can be contained (as described above) or can be used for the manufacturing of such preparations, e.g. water, mixtures of fresh or processed, plant-based or animal-based basic or raw materials (e.g. raw, fried, dried, fermented, smoked and/or cooked meat, bones, cartilage, fish, vegetables, fruits, herbs, nuts, vegetable or fruit juices or pastes or mixtures thereof), digestible or non-digestible carbohydrates (e.g. saccharose, maltose, fructose, glucose, dextrins, amylose, amylopectin, inulin, xylans, cellulose, tagatose), sugar alcohols (e.g. sorbit, erythritol), natural or hardened fats (e.g. tallow, lard, palm fat, coconut fat, hardened plant fat), oils (e.g. sunflower oil, peanut oil, corn oil, olive oil, fish oil, soy oil, sesame oil), fatty acids or salts thereof (e.g. potassium stearate), proteinogenic or non-proteinogenic amino acids and related compounds (e.g. γ-amino butyric acid, taurin), peptides (e.g. glutathione), native or processed proteins (e.g. gelatin), enzymes (e.g. peptidases), nucleic acids, nucleotides, further taste correcting agents or taste modulators for unpleasant taste impressions or non-unpleasant taste impressions, particularly taste modulating substances (e.g. inositol phosphate, nucleotides such as guanosine monophosphate, adenosine monophosphate or other substances such as sodium glutamate or 2-phenoxypropionic acid), emulsifiers (e.g. lecithins, diacylglycerols, gum arabic), stabilizers (e.g. carrageenan, alginate), preservatives (e.g. benzoic acid, sorbinic acid), antioxidants (e.g. tocopherol, ascorbic acid), chelators (e.g. citric acid), organic or inorganic acidifying agents (e.g. malic acid, acetic acid, citric acid, tartaric acid, phosphoric acid), bitter substances (e.g. chinin, caffeine, limonine, amarogentine, humulone, lupolone, catechins, tannins), sweeteners (e.g. saccharin, cyclamate, aspartame, neotame), mineral salts (e.g. sodium chloride, potassium chloride, magnesium chloride, sodium phosphate), enzymatic browning inhibiting substances (e.g. sulfite, ascorbic acid), ethereal oils, plant extracts, natural or synthetic colorings or color pigments (e.g. carotinoids, flavonoids, anthocyanes, chlorophyll and their derivates), spices, trigeminally active substances or plant extracts containing such trigeminally active substances, synthetic, (further) natural or nature identical aroma substance or olfactory substances as well as olfactory correction agents.

Tooth care products (as examples for preparations for oral care according to the invention), generally comprise an abrasive system (abrasive and polishing agents), such as e.g. silicas, calcium carbonates, calcium phosphates, aluminium oxides and/or hydroxyl apatites, surface-active substances such as e.g. sodium lauryl sulfate, sodium lauryl sarcosinate and/or cocamidopropyl betaine, humectants such as e.g. glycerine and/or sorbit, gelling agents, such as e.g. caboxymethyl cellulose, polyethylene glycols, carrageenan and/or Laponite®, sweeteners, such as e.g. saccharin, taste correction agents for unpleasant taste impressions or normally non-unpleasant taste impressions, (or further) taste modulating substances (e.g. inositol phosphate, nucleotides such as guanosine monophosphate, adenosine monophosphate or other substances such as sodium glutamate or 2-phenoxypropionic acid), cooling substances such as e.g. menthol, menthol derivatives (e.g. L-menthol, L-methyl lactate, L-menthylalkyl carbonate, menthone ketals, menthane carbonic acid amides), 2,2,2-trialkyl acetic acid amides (e.g. 2,2-diisopropylpropionic acid methyl amide), icillin derivates, stabilizers and active substances, such as e.g. sodium fluoride, sodium monofluoro phosphate, tin difluoride, quarternary ammonium fluorides, zinc citrate, zinc sulfate, tin pyrophosphate, tin dichloride, mixtures of different pyrophosphates, triclosan, cetylpyridiniumchloride, aluminium lactate, potassium citrate, potassium nitrate, potassium chloride, strontium chloride, hydrogen peroxide, (or further) aromas and/or sodium bicarbonate or olfactory correction agents.

Chewing gums (as further example for preparations for oral care according to the invention), comprise generally a gum base, that means a chewing mass which gets plastic while chewing, sugar of different types, sugar substitutes, sweeteners, sugar alcohols, taste correction agents or taste modulators for unpleasant or normally non-unpleasant taste impressions (or further) taste modulating substances (e.g. inositol phosphate, nucleotides such as guanosine monophosphate, adenosine monophosphate or other substances such as sodium glutamate or 2-phenoxypropionic acid), humectants, gelling agents, emulsifiers, (or further) aromas and stabilizers or olfactory correction agents.

According to a preferred embodiment of the preparation or intermediate good according to the invention as defined above, the preparation or intermediate good according to the invention further comprises one or several (further) flavouring and/or odorous substance(s), wherein the total amount of rotundone containing mixture according to the invention as defined above is sufficient to modify, preferably enhance, one or several taste and/or olfactory impressions of the (further) flavouring and/or odorous substance(s).

Preferred further flavouring and/or odorous substances according to the present invention to be modified, preferably enhanced, are especially present in the following extracts, ethereal oils, concretes, absolues, resins, resinoids, balms or tinctures: amyris oil; angelica seed oil; angelica root oil; anis oil; valerian oil; basil oil; tree moss oil; bay oil; mugwort oil; benzoe resin; bergamot oil; beeswax absolue; birch tar oil; bitter almond oil; savory oil; bucco leaf oil; cabreuva oil;

cade oil; calmus oil; camphor oil; cananga oil; cardamom oil; cascarilla oil; cassia oil; cassie absolue; castoreum absolue; cedar leaf oil; cedar wood oil; cistus oil; citronellol oil, citrus oil; copaiva balm; copaiva balm oil; coriander oil; costus root oil; cumin oil; cypress oil; davana oil; dill weed oil; dill seed oil; oak moss absolue; elemi oil; tarragon oil; eucalyptus citriodora oil; eucalyptus oil; fennel oil; spruce needle oil; galbanum oil; galbanum resin; geranium oil; grapefruit oil; gurjun balm; gurjun balm oil; helichrysum absolue; helichrysum oil; ginger oil; iris root absolue; iris root oil; jasmine absolue; calamus oil; chamomile oil blue; chamomile oil roman; carrot seed oil; cascarilla oil; pine needle oil; spearmint oil; cumin oil; labdanum oil; labdanum absolue; labdanum resin; lavandin absolue; lavandin oil; lavender absolue; lavender oil; lemongrass oil; lovage oil; lime oil distilled; lime oil pressed; linaloe oil; litsea cubeba oil; bay leaf oil; macis oil; marjoram oil; tangerine oil; massoi bark oil; mimosa absolue; musk kernel oil; musk tincture; muscatel sage oil; nutmeg oil; myrrh absolue; myrrh oil; myrten oil; clove leaf oil; clove flower oil; neroli oil; olibanum absolue; olibanum oil; opopanax oil; orange flower absolue; orange oil; origanum oil; palmarosa oil; patchouli oil; perilla oil; perubalm oil; parsley leaf oil; parsley seed oil; petitgrain oil; peppermint oil; pepper oil; allspice oil; pine oil; poley oil; rose absolue; rose wood oil; rose oil; rosemary oil; sage oil dalmantian; sage oil Spanish; celery seed oil; spik lavender oil; star anise oil; styrax oil; tagetes oil; fir needle oil; tea tree oil; turpentine oil; thyme oil; tolu balm; tonka absolue; tuberose absolue; vanilla extract; violet leaf absolue; verbena oil; vetivere oil; juniper berry oil; wine yeast oil; vermouth oil; winter green oil; ylang oil; ysop oil; civet absolue; cinnamon leaf oil; cinnamon bark oil.

Examples for further flavouring and/or odorous substances usable according to the invention are additionally listed in the EU positive list of the implementing provision (EU) Nr. 872/2012, which is valid since 22 Apr. 2013. In this list, the European commission has published a list of aroma substances, which are allowed to be used in the EU in the food industry. Further examples can be found in the Flavor Ingredient Library of the American FEMA (Flavor & Extract Manufacturers Association).

The further flavouring and/or odorous substances that are preferably to be modified, more preferably to be enhanced, within the framework of the present invention, belong to different chemical groups, such as for example:

the group of hydrocarbons, such as e.g. 3-carene; alpha-pinene; beta-pinene; alpha-terpinene; gamma-terpinene; p-cymol; bisabolene; camphene; caryophyllene; cedrene; farnesene; limonene; longifolene; myrcene; ocimene; valencene; (E,Z)-1,3,5-undecatriene;

the group of aliphatic alcohols, such as e.g. hexanol; octanol; 3-octanol; 2,6-dimethyl-heptanol; 2-methylheptanol, 2-methyloctanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7 dimethyl-7-methoxyoctan-2-ol; 9-decenol; 10-undecenol; 4-methyl-3-decen-5-ol;

the group of aliphatic aldehydes and their acetals, such as e.g. hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10 undecenal; (E)-4-decenal; 2-dodecenal; 2,6,10-trimethyl-5,9-undecadienal; heptanal diethylacetal; 1,1-di methoxy-2,2,5-trimethyl-4-hexene;

the group of aliphatic ketones and their oximes, such as e.g. 2-heptanone; 2-octanone; 3-octanone; 2-nonanone; 5-methyl-3-heptanone; 5-methyl-3-heptanone oxime; 2,4,4,7-tetramethyl-6-octen-3-one; the aliphatic sulphur containing compounds, such as e.g. 3-methylthiohexanol; 3-methylthiohexylacetate; 3-mercaptohexanol; 3-mercaptohexylacetate; 3-mercaptohexylbutyrate; 3-acetylthiohexylacetate; 1 menthen-8-thiol;

the group of aliphatic nitriles, such as e.g. 2-nonenic acid nitrile; 2-tridecenic acid nitrile; 2,12-tridecadienic acid nitrile; 3,7-dimethyl-2,6-octadienic acid nitrile; 3,7-dimethyl-6-octenic acid nitrile;

the group of aliphatic carbonic acid esters, such as e.g. (E)- und (Z)-3-hexenyl formiate; ethylaceto acetate; isoamyl acetate; hexyl acetate; 3,5,5-trimethylhexyl acetate; 3-methyl-2-butenyl acetate; (E)-2-hexenyl acetate; (E)- und (Z)-3-hexenyl acetate; octyl acetate; 3-octyl acetate; 1-octen-3-yl acetate; ethyl butyrate; butyl butyrate; isoamyl butyrate; hexyl butyrate; (E)- und (Z)-3-hexenyl isobutyrate; hexyl crotonate; ethyl isovalerate; ethyl-2-methyl pentanoate; ethyl hexanoate; allyl hexanoate; ethyl heptanoate; allyl heptanoate; ethyl octanoate; ethyl-(E,Z)-2,4-decadienoate; methyl-2-octinate; methyl-2-noninate; allyl-2-isoamyloxy-acetate; methyl-3,7-dimethyl-2,6-octadienoate; menthyl lactate (FEMA GRAS 3748); monomethyl succinate (FEMA GRAS 3810); monomethyl glutarate (FEMA GRAS 4006);

the group of acyclic terpene alcohols, such as e.g. citronellol; geraniol; nerol; linalool; lavadulol; nerolidol; farnesol; tetrahydrolinalool; tetrahydrogeraniol; 2,6 dimethyl-7-octen-2-ol; 2,6-dimethyloctan-2-ol; 2-methyl-6-methylen-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; as well as their formiates, acetates, propionates, isobutyrates, butyrates, isovalerates, pentanoates, hexanoates, crotonates, tiglinates, 3-methyl-2-butenoates;

the group of acyclic terpene aldehydes and ketones, such as e.g. geranial; neral; citronellal; 7-hydroxy-3,7-dimethyloctanal; 7-methoxy-3,7-dimethyloctanal; 2,6,10-trimethyl-9-undecenal; geranylaceton; as well as the dimethyl- and diethyl acetals of geranial, neral, 7-hydroxy-3,7-dimethyl-octanal;

the group of cyclic terpene alcohols such as e.g. menthol; isopulegol; alpha-terpineol; terpinenol-4; menthan-8-ol; menthan-1-ol; menthan-7-ol; borneol; isoborneol; linalool oxide; nopol; cedrol; ambrinol; vetiverol; as well as their formiates, acetates, propionates, isobutyrates, butyrates, isovalerates, pentanoates, hexanoates, crotonates, tiglinates, 3-methyl-2-butenoates;

the group of cyclic terpene aldehydes and ketones, such as e.g. menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; nootkatone; dihydronootkatone; alpha-sinensal; beta-sinensal;

the group of cyclic alcohols, such as e.g. 4-tert.-butylcyclo-hexanol; 3,3,5-trimethylcyclo-hexanol; 3-isocamphylcyclo-hexanol; 2,6,9-trimethyl-Z2,Z5,E9-cyclododecatrien-1-ol; 2-isobutyl-4-methyltetrahydro-2H-pyran-4-ol;

the group of cycloaliphatic alcohols, such as e.g. alpha,3,3-trimethylcyclohexylmethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl- 3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

the group of esters of cycloaliphatic carbonic acids, such as e.g. allyl-3-cyclohexylpropionate; allylcyclohexyloxyacetate; methyldihydrojasmonate; methyljasmonate; methyl-2-hexyl-3-oxocyclopentancarboxylate; ethyl-2-ethyl-6,6-dimethyl-2-cyclohexencarboxylate; ethyl-2,3,6,6-tetramethyl-2-cyclohexencarboxylate; ethyl-2-methyl-1,3-dioxolan-2-acetate;

the group of aromatic hydrocarbons, such as e.g. styrene and diphenylmethane;

the group of araliphatic alcohols, such as e.g. benzyl alcohol; 1-phenylethyl alcohol; 2 phenylethyl alcohol; 3-phenyl propanol; 2-phenyl propanol; 2-phenoxy ethanol; 2,2 dimethyl-3-phenyl propanol; 2,2-dimethyl-3-(3-methylphenyl)propanol; 1,1-dimethyl-2-phenylethyl alcohol; 1,1-dimethyl-3-phenyl propanol; 1-ethyl-1-methyl-3-phenyl propanol; 2-methyl-5-phenyl pentanol; 3-methyl-5-phenyl pentanol; 3-phenyl-2-propen-1-ol; 4-methoxybenzyl alcohol; 1-(4-isopropylphenyl)ethanol;

the group of esters of araliphatic alcohols and aliphatic carbonic acids, such as e.g. benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovaleriate; 1-phenylethyl acetate; alpha-trichlormethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

of araliphatic and aliphatic ether and acetals or ketals, such as e.g. 2-phenylethylmethyl ether; 2-phenylethylisoamyl ether; 2-phenylethyl-1-ethoxyethyl ether; phenylacetaldehyde dimethylacetal; phenylacetaldehyde diethylacetal; hydratropaaldehyde dimethylacetal; phenylacetaldehyde glycerinacetal; menthyl methyl ether; menthone glyceryl acetal (FEMA GRAS 3807); menthone glyceryl ketal (FEMA GRAS 3808); menthoxy-1,2-propandiol (FEMA GRAS 3784); menthoxy-2-methyl-1,2-propandiol (FEMA GRAS 3849):

the group of carbonic acid amides, such as e.g. WS-3 (FEMA GRAS 3455), WS-5 (FEMA GRAS 4309), WS-12 (Frescolat® SC-1, FEMA GRAS 4681), WS-23 (FEMA GRAS 3804), (E)-3-benzo[1,3]dioxol-5-yl-N,N-diphenyl-2-propenamide (FEMA GRAS 4788) and 2-(4-methylphenoxy)-N-(1H-pyrazol-3-yl)-N-(thiophen-2-ylmethyl)acetamide (FEMA GRAS 4809); N-(2-isopropyl-5-methylcyclohexyl)cyclopropane carboxamide (FEMA GRAS 4558), 3-(3,4-dimethoxyphenyl)-N-[2-(3,4-dimethoxyphenyl)-ethyl]-acrylamide (FEMA GRAS 4310); (E)-N-[2-(1,3-benzodioxol-5-yl)ethyl]-3-(3,4-dimethoxyphenyl)prop-2-enamide (FEMA GRAS 4773);

the group of carbonates and ureas, such as e.g. menthol ethylene glycol carbonate (FEMA GRAS 3805); menthol propylenglycol carbonate (FEMA GRAS 3806); 3-[3-(2-isopropyl-5-methyl-cyclohexyl) ureido]butyric acid ethylester (FEMA GRAS 4766);

the group of aromatic and araliphatic aldehydes, such as e.g. benzaldehyde; phenylacetaldehyde; 3-phenylpropanal; hydratropa aldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert.-butylphenyl)propanal; 3-(4-tert.-butyl-phenyl)propanal; cinnamic aldehyde; alpha-butyl cinnamic aldehyde; alpha-amyl cinnamic aldehyde; alpha-hexyl cinnamic aldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylendioxyphenyl)propanal;

the group of aromatic and araliphatic ketones, such as e.g. acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl)ethanone; benzophenone;

the group of aromatic and araliphatic carbonic acids and esters thereof, such as e.g. benzoic acid; phenyl acetic acid; methyl benzoate; ethyl benzoate; hexyl benzoate; benzyl benzoate; methyl phenyl acetate; ethyl phenyl acetate; geranyl phenyl acetate; phenylethyl phenyl acetate; methyl cinnamate; ethyl cinnamate; benzyl cinnamate; phenyl ethyl cinnamate; cinnamyl cinnamate; allylphenoxy acetate; methyl salicylate; isoamyl salicylate; hexyl salicylate; cyclohexyl salicylate; cis-3-hexenyl salicylate; benzyl salicylate; phenyl ethyl salicylate; methyl-2,4-dihydroxy-3,6-dimethyl benzoate; ethyl-3-phenyl glycidate; Ethyl-3-methyl-3-phenyl glycidate;

the group of nitrogen containing aromatic compounds, such as e.g. 2,4,6-trinitro-1,3-dime-thyl-5-tert.-butylbenzene; 3,5-dinitro-2,6-dimethyl-4-tert.-butyl acetophenone; cinnamic acid nitrile; 5-phenyl-3-methyl-2-pentenic acid nitrile; 5-Phenyl-3-methylpentanic acid nitrile; methyl anthranilate; methy-N-methyl anthranilate; Schiff bases of methyl anthranilate with 7-hydroxy-3,7-dimethyloctanal, 2-methyl-3-(4-tert.-butylphenyl)propanal or 2,4-dimethyl-3-cyclohexen-carbaldehyde; 6-isopropyl quinoline; 6-isobutyl quinoline; 6-sec.-butyl quinoline; indole; skatole; 2-methoxy-3-isopropylpyrazine; 2-isobutyl-3-methoxypyrazine;

the group of phenols, phenyl ethers and phenyl esters, such as e.g. estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2 ethoxy-5-(1-propenyl)phenol; p-kresyl phenyl acetate;

the group of heterocyclic compounds, such as e.g. 2,5-dimethyl-4-hydroxy-2H-furan-3-one; 2-ethyl-4-hydroxy-5-methyl-2H-furan-3-one; 3-hydroxy-2-methyl-4H-pyran-4-one; 2 ethyl-3-hydroxy-4H-pyran-4-one;

the group of lactones, such as 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; cumarin; 2,3-dihydrocumarin; octahydrocumarin.

According to a further aspect, the present invention relates to a method for manufacturing a composition or intermediate good according to the invention as defined above, comprising or consisting of the following steps:

Providing a rotundone containing mixture as defined above as well as one or several further components, wherein the further component or a further component or several further components is/are preferably selected from the group consisting of flavouring and/or odorous substances, and Mixing of the rotundone containing mixture as defined above with the further component(s).

In the following, the invention is further illustrated by means of examples. Unless otherwise stated, all specifications, particularly percentage and amount specifications, relate to the weight. The weight specification of the ingredients in the application examples is—unless explicitly stated otherwise—described in [g]. The term "Q.S." stands for quantum satis.

EXAMPLES

Manufacturing of Mixtures Containing Rotundone According to the Invention

Example 1a: Dehydratisation if Guaiac Wood Oil with Tartaric Acid 1000 g guaiac wood oil, 50 g tartaric acid and 500 g PEG 600 are provided and heated to 210° C. From 180° C. reaction water is formed, which is continuously distilled off. After 2 h, 50 g tartaric acid are added once again and stirred at 210° C. for another 1.5 h. 766 g of a fraction with an alpha-guaiene content of 18.4% is obtained by distillation of the reaction mixture at a sump temperature of 130° C. and a vacuum of 4.0 mbar.

Example 1b: Dehydratisation of Guaiac Wood Oil with Tartaric Acid 2250 g guaiac wood oil, 112.5 g tartaric acid and 750 g PEG 400 are provided and heated to 210° C. From 180° C. reaction water is formed, which is continuously distilled off. After 2 h, 112.5 g tartaric acid are added once again and stirred at 210° C. for another 1.5 h. 1426 g of a fraction with an alpha-guaiene content of 24.3% is obtained by distillation of the reaction mixture at a sump temperature of 125° C. and a vacuum of 10.0 mbar.

Example 2a: Oxidation of the Guaiene Containing Fraction of Example 1a

The distilled fraction of example 1a is gassed at 100° C. for 27 hours with an air amount of 200 L/h over a glass frit. Subsequently, it is stirred at 120° C. for 1 h without additional air supply in order to destroy formed peroxides before distillation. The peroxide number (POZ) is <30 meq O/kg after this heating step and the mixture is mixed with 430 g triethylcitrate as well as 300 g PEG 600 and distilled over a 30 cm Vigreux column. 850 grams of a fraction with 0.8% rotundone are obtained in total.

GC analysis (semiquantitative: standard tridecane, correction factor triethylcitrate: 2.555): 50.0% triethylcitrate, 0.8% rotundone, 5.2% bulnesene, 3.6% guaiene, 1.0% guaiol, 0.7% bulnesol.

Example 2b: Oxidation of the Guaiene Containing Fraction of Example 1b 1400 g of the distillation fraction of example 1b are reacted for 24 hours at 100° C. with an air amount of 120 L/h in a bubble column. Thereby, the content of rotundone and guaiene is determined by gas chromatographic analysis for reaction control. Subsequently, it is stirred at 120° C. for 2 h without any further air supply in order to destroy formed peroxides before distillation. After this heating step, the peroxide number (POZ) is <30 meq O/kg. Subsequently, 700 g of the reaction mixture are mixed with 500 g trethylcitrate and 500 g PEG 400 and fractionary distilled over a 30 cm Vigreux column. The fraction containing or consisting of the rotundone containing mixture according to the invention was collected at a temperature of 130° C.-135° C. at a vacuum of 0.2-0.8 mbar. 252.2 g of the rotundone containing mixture were obtained in total.

GC analysis (semiquantitative: standard tridecane, correction factor triethylcitrate: 2.555): 69.2% triethylcitrate, 1.0% rotundone, 0.2% bulnesene, 0.01% guaiene, 2.0% guaiol, 1.4% bulnesol.

Intermediate Goods and Preparations According to the Invention

Application Example 1: Improvement of Citrus Oils

|  | Type Lime | Type Tangerine | Type Orange | Type Grapefruit | Type Lemon |
|---|---|---|---|---|---|
| Lime oil distilled | Q.S. | | | | |
| Tangerine oil red italian | | Q.S. | | | |
| Orange oil brazilian | | 30.000 | Q.S. | Q.S. | |
| Orange essence oil florida | | | 50.000 | | |
| Grapefruit oil white | | | | 60.000 | |
| Lemon oil italian | | | | | Q.S. |
| TERPINEOL. ALPHA- | 25.000 | 0.200 | 0.400 | 0.150 | 1.000 |
| TERPINOLENE | 5.000 | 1.000 | | 0.010 | 1.000 |
| TERPINEOL. GAMMA- | 4.000 | | | | |
| TERPINENE. GAMMA- | 3.000 | 15.000 | | | 16.000 |
| CARYOPHYLLENE | 2.500 | 0.100 | 0.040 | 0.400 | 1.500 |
| NERYL ACETATE | 2.500 | | | | 3.000 |
| TERPINENOL. 4- | 4.000 | 0.050 | 0.100 | | 0.100 |
| FENCHOL | 2.000 | | | | |
| GERANYL ACETATE | 0.050 | | | 0.080 | 1.600 |
| CYMENE. P- | 1.000 | 1.000 | | 0.200 | 0.200 |
| Citral | 0.500 | | 0.500 | 0.200 | 20.000 |
| LINALOOL | 0.500 | 0.100 | 3.000 | 0.400 | 0.500 |
| VALENCENE fraction ex orange | | | 1.000 | 0.300 | 0.500 |
| EUCALYPTOL | 0.500 | | | | 0.200 |
| ALDEHYDE C12 | 0.300 | | 0.200 | 0.050 | 0.000 |
| CARYOPHYLLENE OXIDE | 0.300 | | 0.100 | | |
| CAPRINIC ACID | | | | 0.100 | 0.200 |
| CEDRENE nat. | 0.200 | | | | |
| OCIMENE | 0.200 | | | 0.500 | 0.500 |

-continued

|  | Type Lime | Type Tangerine | Type Orange | Type Grapefruit | Type Lemon |
|---|---|---|---|---|---|
| Camphor oil | 0.100 |  |  |  | 0.050 |
| ALDEHYDE C10 | 0.200 | 0.050 | 1.000 | 0.600 | 0.200 |
| ALCOHOL C 10 | 0.100 | 0.010 | 0.080 | 0.020 | 0.010 |
| BORNEOL ISO- | 0.100 |  |  |  |  |
| Borneol | 0.050 |  |  |  | 0.020 |
| NEROL | 0.060 | 0.010 | 0.050 |  | 0.400 |
| CARVEOL L TRANS | 0.050 | 0.010 | 0.250 | 0.040 |  |
| MYRCENE |  | 1.800 | 1.800 | 1.800 | 0.300 |
| PINENE. BETA- |  | 1.500 |  | 0.250 | 0.250 |
| PHELLANDRENE ALPHA | 0.050 | 0.050 | 1.000 | 0.050 |  |
| HEXENAL. 2E- |  |  | 0.020 |  |  |
| ALCOHOL C 6 |  |  | 0.010 |  |  |
| ALDEHYDE C 7 |  |  |  |  |  |
| ALDEHYDE C 6 |  |  | 0.100 |  |  |
| ETHYL METHYL-BUTYRATE-2 |  |  | 0.020 |  |  |
| ETHYL BUTYRATE |  |  | 0.200 |  |  |
| METHYL BUTYRATE |  |  |  |  |  |
| ETHYL CAPRONATE |  |  |  |  |  |
| OCTYL ACETATE. 1- |  |  | 0.070 | 0.100 | 0.020 |
| LINALOOL OXIDE |  |  |  |  |  |
| ETHYL CAPRYLATE |  |  | 0.020 |  |  |
| ALCOHOL C 8 |  | 0.050 | 0.500 | 0.200 |  |
| HEXENOL. 3Z- |  |  |  |  |  |
| HEPTYL ACETATE |  |  |  | 0.040 |  |
| OCTANAL. 6-METHYL- |  | 0.000 |  | 0.050 | 0.000 |
| ALDEHYDE C 9 |  | 0.010 | 0.200 | 0.100 | 0.400 |
| CITRONELLAL |  | 0.010 | 0.150 | 0.050 | 0.500 |
| ALCOHOL C 7 |  |  |  |  |  |
| PINENE. ALPHA- |  | 3.000 |  | 1.000 | 0.500 |
| FENCHONE | 0.200 |  |  |  |  |
| ALDEHYDE C 8 |  | 0.100 | 1.000 | 0.500 | 0.020 |
| PHELLANDRENE BETA |  | 1.000 |  |  | 0.700 |
| CARENE. DELTA-3- |  |  |  |  |  |
| CAMPHENE | 0.020 |  |  |  |  |
| SINENSAL fraction ex orange |  |  | 0.500 |  |  |
| THYMOL |  | 0.100 |  |  |  |
| CAPRYLIC ACID |  |  | 0.100 | 0.050 | 0.050 |
| DODECENAL. 2E- |  | 0.010 |  |  |  |
| PERILLA ALDEHYDE replacement |  | 0.050 | 0.150 | 0.040 | 0.100 |
| CITRONELLOL |  | 0.010 | 0.070 |  | 0.050 |
| ALCOHOL C 9 |  |  | 0.100 |  | 0.050 |
| DIMETHYLANTHRANILATE |  | 0.500 |  |  |  |
| CARVYL ACETATE. TRANS- |  |  |  | 0.050 |  |
| NOOTKATONE |  |  | 0.100 | 0.400 |  |
| ALDEHYDE C11 |  |  |  |  | 0.050 |
| CITRONELLYL ACETATE |  |  |  |  | 0.130 |
| PALMITINIC ACID |  |  |  | 0.080 | 0.350 |
| DECADIENAL. 2E.4E- |  |  |  |  |  |
| GERANIOL |  |  | 0.030 | 0.020 | 0.200 |
| LINALYL ACETATE |  |  |  |  |  |
| DECENAL. 2E- |  |  | 0.020 |  |  |
| Menthenethiol-1.8 1% in limonene |  |  |  | 0.700 |  |
| HOTRIENOL |  |  |  |  | 0.020 |
| Mixture of Example 2b | 0.007 or 0.020 or 0.060 or 0.140 | 0.010 or 0.050 or 0.100 or 0.150 | 0.004 or 0.008 or 0.025 or 0.050 | 0.04 or 0.10 or 0.30 or 0.50 | 0.004 or 0.008 or 0.025 |
| Sum | 100.0 | 100.0 | 100.0 | 100.0 | 100.0 |

The obtained mixtures are used preferably in a dosage of 10-100 ppm, more preferably 20-50 ppm, in foods and beverages. The impact was increased significantly for all oils by addition of the mixture obtained in example 2b, and further positive changes in the complete flavor profile occurred. In case of the lime oil, the camphor like notes are enhanced und the profile gets spicy notes. In case of the tangerine oil, the ripening notes are slightly suppressed and the shelled, fresh aspects are enhanced. For the orange oil, the addition of the mixture obtained in example 2b leads to a fuller profile with more ripe and fruity notes. For grapefruit oil, the woody notes emerge stronger after addition of the mixture obtained in example 2 b, moreover the profile becomes fruitier and the sulphur notes are enhanced. For the lemon oil, the whole profile is enhanced as well as fresh and flowery notes are emphasized.

Application Example 2: Hazelnut Aroma

| | |
|---|---|
| ACATHYLPYRIDINE | 5.00 |
| BENZALDEHYDE DD | 1.00 |
| CAPRINIC ACID NAT. | 0.50 |
| DECALACTONE DELTA | 0.20 |
| DIMETHYLPYRAZINE-2,3 | 0.40 |
| DIMETHYLPYRAZINE-2,5 | 0.40 |
| FILBERTONE | 0.10 |
| FURANEOL 15% ALC | 10.00 |
| ANISIC ALDEHYDE | 0.20 |
| METHOXYMETHYLPYRAZINE-2,3 | 0.20 |
| METHYLCYCLOPENTENOLONE-3,2,2 | 0.05 |
| PENTANDIONE-2,3 | 1.00 |
| HELIOTROPIN/PIPERONAL NAT. | 0.50 |
| HEXENOL CIS-3 | 0.50 |
| ISOBUTYRIC ALDEHYDE | 2.00 |
| MALTOL | 1.00 |
| METHYL ETHYL PYRAZINE-2,3 | 1.00 |
| NONENAL TRANS-2 1% | 0.20 |
| PHENYL ETHYL ALCOHOL | 0.50 |
| TRIMETHYL PYRAZINE-2,3,5 | 0.50 |
| VANILLA EXTRACT | 10.00 |
| HAZELNUT DISTILLATE 3-f. 60 VP | 100.00 |
| Mixture of Example 2 b | 0.02 or 0.06 or 0.2 or 0.4 |
| ETHANOL 95% | Q.S. |
| Sum | 1000.00 |

For evaluation, typically 80 g of sugar are mixed with 0.1 g of the hazelnut aroma and diluted to 1 L with water. In comparison to the sample without the mixture according to the invention of example 2b, the impact is significantly enhanced, the profile is rounded and the nut nougat note is emphasized more.

Application Example 3: Strawberry Aroma

| | |
|---|---|
| ACETIC ACID | 5 |
| ACETYL METHYL CARBINOL | 1 |
| BUTYRIC ACID | 5 |
| CAPRONIC ACID NAT. FOR SWEET & FRUITY | 10 |
| CAPRYLIC ACID | 2 |
| DECALACTONE GAMMA | 4 |
| DIMETHYL ANTHRANILATE EXTRA | 0.2 |
| ETHYL BUTYRATE | 20 |
| ETHYL CAPROATE | 5 |
| ETHYL METHYL BUTYRATE-2 | 5 |
| FURANEOL 15% PG | 100 |
| HEDIONE | 0.2 |
| HEXENOL CIS-3 | 10 |
| MALTOL | 3 |
| METHYL CINNAMATE | 4 |
| METHYL BUTYRIC ACID-2 | 8 |
| METHYL PENTENIC ACID-2,2 | 2 |
| STRAWBERRY RECOVERY | 50 |
| Mixture of example 2a | 0.002 or 0.005 or 0.01 or 0.03 |
| ETHYL ALCOHOL 96.5% VOL | Q.S. |
| Sum | 1000.0 |

For evaluation, typically 80 g of sugar, 1.5 g of citric acid are mixed with 0.4 g of the strawberry aroma and diluted to 1 L with water. In comparison to the sample without the mixture according to the invention of example 2a, the impact is significantly enhanced, the ester notes emerge more strongly and the profile in general gets a more ripened note that reminds of forest fruit.

Application Example 4: Raspberry Aroma

| | |
|---|---|
| ACETALDEHYDE 50% | 5 |
| ALCOHOL C 6 | 0.5 |
| ALDEHYDE C 6 | 1 |
| BUTYRIC ACID | 0.1 |
| CAPRONIC ACID | 0.1 |
| DAMASCENONE | 0.5 |
| DAMASCONE BETA | 0.5 |
| ACETIC ACID E260 | 20 |
| ETHYL ACETATE | 0.3 |
| ETHYL BUTYRATE | 0.3 |
| ETHYL CAPRONATE | 0.3 |
| FRAMBINON ® | 5 |
| FURANEOL 15% PG | 25 |
| GERANIOL | 0.25 |
| HEXENAL TRANS-2 | 0.5 |
| HEXENOL CIS-3 | 25 |
| HEXENYL ACETATE CIS-3 | 1 |
| HEXYL ACETATE | 1 |
| IONONE ALPHA | 2 |
| IONONE BETA FG | 2 |
| ISOAMYL ACETATE | 0.5 |
| ISOBUTYL ACETATE | 1 |
| MACROLIDE ® SUPRA 1% PG | 0.5 |
| MALTOL | 5 |
| PHENYL ETHYL ALCOHOL | 0.2 |
| RASPBERRY DISTILLATE | 150 |
| Mixture of example 2a | 0.002 or 0.005 or 0.01 or 0.03 |
| PROPYLENE GYLCOL | Q.S. |
| Sum | 1000.0 |

For evaluation, typically 80 g of sugar, 1.5 g of citric acid are mixed with 0.5 g of the raspberry aroma and diluted to 1 L with water. In comparison to the sample without the mixture according to the invention of example 2a, the impact is significantly enhanced, the flowery notes reminding of ionone are enhanced and the profile gets a woodier character.

Application Example 5: Mango Aroma (Type Tropical)

| | |
|---|---|
| ACETYLMETHYLCARBINOL | 0.2 |
| ALLYL CAPROATE | 3 |
| BUCCOLEAVE OIL | 0.1 |
| BUTYRIC ACID | 0.1 |
| CAPRYLIC ACID | 1 |
| CARYOPHYLLEN | 2 |
| DECALACTONE DELTA | 1 |
| DECALACTONE GAMMA | 3 |

-continued

| | |
|---|---|
| DIPHENYL OXIDE | 0.5 |
| DMS/DIMETHYLSULFIDE | 1 |
| ETHANETHIOL 1% TRIA | 0.02 |
| ETHYL ACETATE | 2 |
| ETHYL BUTYRATE | 15 |
| ETHYL CAPROATE | 1 |
| ETHYL CAPRYLATE | 0.5 |
| ETHYL METHYL BUTYRATE-2 | 2 |
| ETHYL VALERATE | 1 |
| FURANEOL 15% PG | 5 |
| HEXENOL CIS-3 | 2 |
| HEXENYL ACETATE CIS-3 | 1 |
| HEXYL CAPROATE | 0.5 |
| IONONE BETA | 0.02 |
| ISOPROPYLMETHYL-THIAZOLE-2,4 1% TRI | 0.1 |
| LINALOOL | 0.5 |
| MALTOL | 5 |
| THIOHEXANOL-3 1% | 0.01 |
| THIOHEXYL ACETATE 1% | 0.01 |
| MYRCENE | 1 |
| OCIMENE | 1 |
| OCTALACTONE GAMMA | 0.5 |
| ORANGE OIL FLORIDA | 1 |
| TERPINENOL-4 NAT. | 0.1 |
| TERPINOLENE | 0.5 |
| THIOMENTHANONE-8,3 1% TRIA | 2 |
| MANGO RECOVERY | 30 |
| Mixture of example 2b | 0.005 or 0.02 or 0.05 or 0.1 |
| PROPYLENE GLYCOL-1,2 | Q.S. |
| Sum | 1000.0 |

For evaluation, typically 80 g of sugar, 1.5 g of citric acid are mixed with 0.5 g of the mango aroma and diluted to 1 L with water. In comparison to the sample without the mixture according to the invention of example 2b, the impact is significantly enhanced, the whole profile seems stronger, more characteristic und has more shelled, terpenic notes, however, the sulfuric notes are particularly enhanced.

Application Example 6: Pear Aroma

| | |
|---|---|
| ACETALDEHYDE | 10 |
| ALCOHOL C6 | 20 |
| ACETIC ACID | 2 |
| BUTYL ACETATE | 5 |
| ETHYL ACETATE | 5 |
| ETHYL BUTYRATE | 3 |
| ETHYL CAPRYLATE | 0.5 |
| ETHYLDECADIENOATE | 1 |
| FURANOL 15% PG | 1 |
| GERANYL BUTYRATE | 1 |
| HEXENAL TRANS-2 | 10 |
| HEXYL ACETATE | 20 |
| HEXENYL ACETATE CIS-3 | 15 |
| ISOAMYL ACETATE | 20 |
| ISOBUTYL ACETATE | 5 |
| METHYL METHYL BUTYRATE | 10 |
| PEAR JUICE CONC. 70BX CLEAR | 100 |
| PEAR WILLIAMS BRANDY 40% VOL | 200 |
| ETHYL ALCOHOL 96.5% VOL | 200 |
| Mixture of example 2b | 0.02 or 0.04 or 0.1 or 0.2 |
| PROPYLENE GLYCOL-1,2 | Q.S. |
| Sum | 1000.0 |

For evaluation, typically 80 g of sugar, 1.5 g of citric acid are mixed with 0.1 g of the banana aroma and diluted to 1 L with water. In comparison to the sample without the mixture according to the invention of example 2b, the impact is significantly enhanced, the estery, ripe notes are emphasized and the aroma more reminds of Williams Christ pears.

Application Example 7: Banana Aroma

| | |
|---|---|
| ACETYLMETHYLCARBINOL | 1 |
| BUTYL ACETATE | 1 |
| BUTYRIC ACID | 0.5 |
| CINNAMIC ALDEHYDE | 0.3 |
| CITRAL FF | 0.1 |
| ETHYL ACETATE | 0.5 |
| ETHYL BUTYRATE | 0.5 |
| EUGENOL NAT. | 0.2 |
| FURANEOL 15% | 3 |
| GERANYL ACETATE | 0.04 |
| HEXENAL TRANS-2 | 2 |
| ISOAMYL ACETATE MIX | 20 |
| ISOAMYL ALCOHOL | 5 |
| ISOAMYL BUTYRATE | 5 |
| ISOAMYL ISOVALERATE | 2 |
| ISOBUTYL ACETATE | 1 |
| METHYL HEPTIN CARBONATE | 0.05 |
| NONADIENAL TRANS,CIS-2,6 1% | 0.02 |
| ORANGE OIL | 0.2 |
| VANILLIN | 0.5 |
| BANANA RECOVERY | 50 |
| Mixture of example 2a | 0.004 or 0.008 or 0.02 |
| PROPYLENE GLYCOL-1,2 | Q.S. |
| Sum | 1000.0 |

For evaluation, typically 80 g of sugar and 0.4 g of the pear aroma are mixed and diluted to 1 L with water. In comparison to the sample without the mixture according to the invention of example 2a, the impact is significantly enhanced and the woody, eugenol-like aspects are highlighted.

Application Example 8: Chocolate Aroma

| | |
|---|---|
| ACETYLMETHYLCARBINOL | 2 |
| ANISIC ALDEHYDE 1% | 0.5 |
| BENZALDEHYDE 10% | 0.2 |
| BUTYRIC ACID | 0.05 |
| CINNAMIC ALDEHYDE | 0.1 |
| CI NNAMYL ACETATE | 1 |
| CRESOL PARA 0, 1% | 0.2 |
| DECALACTONE DELTA | 0.2 |
| DIMETHYLETHYLPYRAZINE-3,5(6),2 | 0.2 |
| DIMETHYLPYRAZINE-2,3 | 0.2 |
| DIMETHYLPYRAZINE-2,5 | 0.1 |
| DIMETHYLPYRAZINE-2,6 | 0.05 |
| DODECALACTONE DELTA | 0.1 |
| ETHYL CAPROATE | 0.05 |
| FURANEOL 15% | 5 |
| GUAIACOL 1% | 0.5 |
| ISOAMYL ALCOHOL | 2 |
| ISOBUTYRALDEHYDE | 0.5 |
| ISOVALERIC ACID NAT. | 0.1 |
| ISOVALERIC ALDEHYDE | 2 |
| METHYLCYCLOPENTENOLONE-3,2,2 | 2 |
| METHYLGUAIACOL-4 | 0.1 |
| METHYLPHENYLHEXENAL TRANS-5,2,2 | 2 |
| METHYLPYRAZINE-2 | 0.1 |
| PHENYL ACETALDEHYDE | 1 |
| PHENYLACETIC ACID | 2 |
| ETHYL PHENYL ACETATE | 0.5 |
| PHENYL ETHYL ALCOHOL | 0.5 |
| TRIMETHYLPYRAZINE-2,3,5 | 0.5 |
| VANILLA EXTRACT BOURBON 3X | 5 |
| VANILLIN | 50 |

| | |
|---|---|
| CACAO EXTRACT | 50 |
| TRIACETIN | 250 |
| Mixture of example 2b | 0.004 or 0.02 or 0.04 |
| PROPYLENE GLYCOL-1,2 | 621.25 |
| Sum | 1000.0 |

For evaluation, typically 80 g of sugar and 0.5 g of the chocolate aroma are mixed and diluted to 1 L with water. In comparison to the sample without the mixture according to the invention of example 2b, the impact is significantly enhanced, moreover the aroma appears fuller and more complex and the phenolic notes are emphasized more.

Application Example 9: Pineapple Aroma

| | |
|---|---|
| ACETALDEHYDE NAT. 50% TRIC | 5 |
| ACETIC ACID | 5 |
| ALLYL CAPROATE | 5 |
| CAPRONIC ACID | 0.5 |
| ETHYL BUTYRATE | 5 |
| ETHYL CAPROATE | 8 |
| ETHYL ISOVALERATE | 2 |
| ETHYL METHYL THIOPROPIONATE-3 | 0.5 |
| FURANEOL 15% PG | 20 |
| HEXENOL CIS-3 | 0.5 |
| ISOAMYL ACETATE | 5 |
| ISOAMYL ISOVALERATE | 2 |
| METHYLMETHYLTHIOPROPIONATE-3 NAT. | 1 |
| PINEAPPLE RECOVERY CONC. | 50 |
| Mixture of example 2b | 0.007 or 0.03 or 0.07 |
| PROPYLENE GLYCOL | Q.S. |
| Sum | 1000.0 |

For evaluation, typically 80 g of sugar, 1.5 g of citric acid are mixed with 0.3 g of the pineapple aroma and diluted to 1 L with water. In comparison to the sample without the mixture according to the invention of example 2b, the impact is significantly enhanced, moreover the aroma appears fuller and more complex and the estery notes are emphasized more.

Application Example 10: Rum Aroma

| | |
|---|---|
| ACETALDEHYDE DIETHYLACETAL | 25 |
| ACETALDEHYDE NATURAL | 25 |
| ACETIC ACID | 50 |
| ACETOIN | 1 |
| BUTYRIC ACID | 1 |
| CAPRINIC ACID | 1 |
| CAPRONIC ACID | 0.1 |
| DAMASCENONE BETA | 0.05 |
| ETHYL ACETATE | 50 |
| ETHYL ALCOHOL 96.5% VOL | 80 |
| ETHYL CAPRYLATE | 0.6 |
| ETHYL FORMATE | 10 |
| ETHYL BUTYRATE | 0.1 |
| EUGENOL | 0.05 |
| GUAIACOL | 0.02 |
| ISOBUTANOL | 50 |
| ISOVALERALDEHYDE | 0.5 |
| ISOVALERIC ACID | 0.5 |
| METHYLBUTANOL-3 | 150 |
| PHENYL ETHYL ALCOHOL | 2 |
| OAK WOOD EXTRACT | 10 |
| RUM JAMAICA 75% VOL | 100 |

| | |
|---|---|
| VANILLA EXTRACT | 5 |
| Mixture of example 2b | 0.005 or 0.01 or 0.075 or 0.2 |
| WATER | Q.S. |
| Sum | 1000.0 |

For evaluation, typically 20 g of sugar, 2 g of glycerin, 1 g of caramel syrup as well as 417 ml of ethanol (96.5%) are mixed with 1.2 g of the rum aroma and diluted to 1 L with water. In comparison to the sample without the mixture according to the invention of example 2b, the impact is significantly enhanced, moreover the aroma appears fuller and more complex, the oak wood notes are enhanced and the whole profile more reminds of barrel-stored qualities.

Application Example 11: Whiskey Aroma

| | |
|---|---|
| Caprinic acid | 130 |
| Caprylic acid | 10 |
| Ethyl acetate | 100 |
| Ethyl caprinate | 50 |
| Ethyl capronate | 2 |
| Ethyl caprylate | 10 |
| Isobutanol | 248 |
| Methylbutanol-3 | 198 |
| Ethyl alcohol | 247.98 |
| Wine yeast oil | 4 |
| Mixture of example 2b | 0.02 |
| Sum | 1000.0 |

By addition of 0.005 or 0.01% to a present whiskey, the impact is significantly enhanced, moreover the aroma appears fuller and rounder, the oak wood notes are enhanced und the whole profile reminds more of barrel-stored qualities.

Application Example 12: Nutmeg Aroma

| | |
|---|---|
| Eugenol | 5 |
| Linalool | 12 |
| Pinene alpha | 180 |
| Pinene beta | 50 |
| Terpineol alpha | 2.5 |
| Nutmeg oil | 50 |
| Ethyl alcohol | 700.45 |
| Mixture of example 2a | 0.05 |
| Sum | 1000.0 |

Application Example 13: Pepper Aroma

| | |
|---|---|
| Pepper oil black | 10 |
| Piperine | 0.5 |
| Ethyl alcohol | 989.4 |
| Mixture of example 2b | 0.1 |

This pepper aroma can be used in dosages from 0.05 or 0.1%. In comparison to the sample without the mixture according to the invention, the impact is significantly enhanced, moreover the aroma appears more typical and fresher.

Application Example 14: Onion Aroma

| | |
|---|---|
| DIMETHYLSULFIDE | 2.00 |
| DIPROPYLDISULFIDE | 13.00 |
| ISOBUTYRIC ALDEHYDE | 4.00 |
| METHYLPROPYLDISULFIDE | 7.00 |
| ONION OIL | 2.00 |
| THIOPENTANONE-3,2 | 3.00 |
| Mixture of example 2b | 0.01 or 0.05 or 0.10 |
| TRIACETIN | Q.S. |
| Sum | 1000.00 |

For evaluation, typically 3 g of salt and 0.1 g of the onion aroma are mixed and diluted to 1 L with warm water. In comparison to the sample without the mixture according to the invention of example 2b, the impact is significantly enhanced, moreover the aroma appears fresher and more balanced.

Application Example 15: Potato Aroma

| | |
|---|---|
| ACETYLMETHYLCARBINOL | 20.00 |
| ACETYLTHIAZOL-2 | 2.00 |
| ALDEHYDE C 6 | 2.00 |
| ALDEHYDE C14 | 6.00 |
| ALCOHOL C 6 | 4.00 |
| BUTYRIC ACID | 5.00 |
| DECADIENAL TRANS,TRANS-2,4 | 0.10 |
| DIMETHYLPYRAZINE-2,3 | 2.00 |
| DIMETHYLSULFIDE | 5.00 |
| DODECALACTONE DELTA | 8.00 |
| HEPTANONE-2 | 2.00 |
| HEPTENAL TRANS-2 | 0.50 |
| ISOBUTYRIC ALDEHYDE | 10.00 |
| ISOPROPYLMETHOXYPYRAZINE-2,3 0.1% TRIA | 10.00 |
| METHOXYETHYLPYRAZINE-2,3 0.1% TRIA | 10.00 |
| METHYLGUAIACOL-4 | 0.20 |
| METHYLMERCAPTAN | 0.10 |
| METHYLTHIOPROPANAL-3 | 4.00 |
| OCTENOL-1,3 | 0.10 |
| PHENYL ACETALDEHYDE | 0.50 |
| Mixture of example 2b | 0.01 or 0.05 or 0.10 |
| TRIACETIN | Q.S. |
| Sum | 1000.00 |

For evaluation, typically 3 g of salt and 0.2 g of the potato aroma are mixed and diluted to 1 L with warm water. In comparison to the sample without the mixture according to the invention, the impact is significantly enhanced, moreover the whole aroma appears more intense.

Application Example 16: Mushroom Aroma

| | |
|---|---|
| ALCOHOL C 8 | 2.00 |
| BENZALDEHYDE DD | 1.00 |
| CAPRINIC ACID | 5.00 |
| CAPRYLIC ACID | 4.00 |
| FENCHOL | 0.10 |
| FURFURYL ALCOHOL | 1.50 |
| ISOVALERIC ACID | 0.50 |
| METHYLTHIOPROPANAL-3 | 0.10 |
| OCTANOL-3 | 0.60 |
| OCTENOL-1,3 | 40.00 |
| OCTENON-1,3 | 0.40 |
| OCTENYL ACETATE-1,3 | 0.60 |
| MUSHROOM (STONE-)-EXTRACT | 5.00 |
| TERPINENOL-4 | 8.00 |
| TRIMETHYLPYRAZINE-2,3,5 | 1.00 |
| Mixture of example 2b | 0.01 or 0.05 or 0.10 |
| TRIACETIN | Q.S. |
| Sum | 1000.0 |

For evaluation, typically 3 g of salt and 0.2 g of the mushroom aroma are mixed and diluted to 1 L with warm water. In comparison to the sample without the mixture according to the invention of example 2b, the impact is significantly enhanced, moreover woody and earthy notes are enhanced and the whole aroma shifts in the direction of wild mushroom.

Application Example 17: Carrot Aroma

| | |
|---|---|
| ACETYLMETHYLCARBINOL | 1.00 |
| ALDEHYDE C 6 | 0.10 |
| ALDEHYDE C 8 | 0.10 |
| ALDEHYDE C10 | 0.10 |
| BAY LEAF OIL | 3.00 |
| BENZALDEHYDE | 1.00 |
| CAPRONIC ACID | 1.00 |
| CAPRYLIC ACID | 2.00 |
| CARENE DELTA-3 | 0.20 |
| CARYOPHYLLENE | 12.00 |
| IONONE BETA | 1.20 |
| ISOVALERIC ACID | 0.70 |
| CARROT SEED OIL | 5.00 |
| PALMAROSA OIL | 1.00 |
| PHELLANDRENE FRACTION EX EUCALYTUS OIL | 7.00 |
| PINENE BETA | 1.60 |
| Mixture of Example 2a | 0.02 or 0.05 or 0.10 |
| TRIACETIN | Q.S. |
| Sum | 1000.0 |

For evaluation, typically 3 g of salt and 0.4 g of the carrot aroma are mixed and diluted to 1 L with warm water. In comparison to the sample without the mixture according to the invention of example 2a, the impact is significantly enhanced, moreover the aroma appears sweeter and more ripe.

Application Example 18: Paprika Aroma (Red)

| | |
|---|---|
| PAPRIKA JUICE CONC. RED 65BX SAUTEED | 50.00 |
| DIMETHYLSULFIDE | 2.00 |
| ETHYL ISOBUTYRATE | 3.00 |
| ETHYL METHYL BUTYRATE-2 | 1.00 |
| FURANEOL | 35.00 |
| GUAIACOL | 0.30 |
| HEXENAL TRANS-2 1% TRIA | 10.00 |
| IONONE BETA FG | 2.50 |
| ISOBUTYLMETHOXYPYRAZINE-3,2 1% TRIA | 37.00 |
| ISOPROPYLMETHOXYPYRAZINE-2,3 1% TRIA | 1.00 |
| METHOXYMETHYLPROPYLPYRAZINE 1% TRIA | 12.00 |
| METHYL ISOVALERATE | 1.50 |
| METHYL METHYL BUTYRATE-2 | 2.00 |
| PHENYLACETIC ACID | 13.00 |
| PROPIONIC ACID | 60.00 |
| Mixture of example 2b | 0.02 or 0.05 or 0.10 |
| TRIACETIN | Q.S. |
| Sum | 1000.0 |

For evaluation, typically 3 g of salt and 0.2 g of the paprika aroma are mixed and diluted to 1 L with warm water.

In comparison to the sample without the mixture according to the invention of example 2b, the impact is significantly enhanced, moreover the aroma appears more ripe and juicier and has overall more taste deepness and complexity.

Application Example 19: Tomato Aroma

| | |
|---|---|
| ALDEHYDE C 6 | 2.00 |
| ALCOHOL C 6 | 1.20 |
| CLOVE LEAF OIL | 5.00 |
| DAMASCENONE | 0.40 |
| DIMETHYL SULFIDE | 4.50 |
| ETHYL SALICYLATE | 0.20 |
| FURANEOL | 1.00 |
| GERANYL BUTYRATE | 2.00 |
| GUAIACOL | 0.20 |
| HEXENOL CIS-3 | 0.40 |
| IONONE BETA | 1.00 |
| ISOBUTYL THIAZOL-2 | 0.20 |
| LINALOOL | 0.10 |
| METHYL HEPTENONE-6,5,2 | 0.60 |
| PHENYL ETHYL ALCOHOL | 30.00 |
| Mixture of example 2b | 0.01 or 0.05 or 0.10 |
| TRIACETIN | Q.S. |
| Sum | 1000.0 |

For evaluation, typically 3 g of salt and 0.1 g of the tomato aroma are mixed and diluted to 1 L with warm water. In comparison to the sample without the mixture according to the invention of example 2b, the impact is significantly enhanced, moreover the aroma appears more ripe and juicier and has overall more taste deepness and complexity.

Application Example 19a: Spray-Dried Tomato Aroma

| | |
|---|---|
| Water | 1135.00 |
| Maltodextrin | 665.00 |
| Tomato aroma of application example 19 | 200.00 |
| Starch | 165.00 |

The compounds are mixed and subsequently spray-dried.

Application Example 20: Spearmint Aroma

| | |
|---|---|
| Menthol | 300 |
| Carvone | 200 |
| Spearmint oil type native | 200 |
| Anethol | 50 |
| Peppermint oil Mentha arvensis rectified | 100 |
| Peppermint oil Mentha piperita type Willamette | Q.S. |
| Mixture of example 2b | 0.6 |
| Sum | 1000.0 |

Application Example 21: Chewing Gum with Spearmint Aroma

| | | |
|---|---|---|
| Chewing gum base | 21 | 30 |
| Glycerin | 0.5 | 1 |
| Glucose syrup | 16.5 | — |
| Powdered sugar | Q.S. | — |
| Sorbitol (in powder form) | — | Q.S. |
| Palatinit | — | 9.5 |
| Xylitol | — | 2 |
| Mannitol | — | 3 |
| Aspartame | — | 0.1 |
| Acesulfame K | — | 0.1 |
| Emulgum ™ (emulsifier) | — | 0.3 |
| Sorbitol 70%, in water | — | 14 |
| Aroma type spearmint (Application example 20) | 1 | 1.4 |
| Sum | 100.0 | 100.0 |

Application Example 22: Mouthwash (without Alcohol) with Spearmint Aroma

| | |
|---|---|
| Cremophor RH 455 | 1.8 |
| Deionized water | Q.S. |
| Sorbitol 70% | 10 |
| Sodium fluoride | 0.18 |
| Sodim saccharin 450 | 0.1 |
| Solbrol M Sodium salt | 0.15 |
| Pellitorine-solution PLM (enthaltend 10% Pellitorin) | — |
| Arom type spearmint (Application example 20) | 0.2 |
| Sum | 100.0 |

Application Example 23: Mouthwash (with Alcohol) with Spearmint Aroma

| | | |
|---|---|---|
| Ethyl alcohol 96% | 10 | 7 |
| Cremophor CO 40 | 1 | 1 |
| Benzoic acid | 0.1 | 0.1 |
| Deionized water | Q.S. | Q.S. |
| Sorbitol 70% | 5 | 5 |
| Sodium saccharin 450 | 0.07 | 0.05 |
| L-Blue 5000 (1% in water) | 0.1 | 0.1 |
| 1,2-Propylene glycol | — | 3 |
| Cetylpyridinium chloride | — | 0.07 |
| Hydrogen peroxide (35% $H_2O_2$ in water) | — | 4 |
| Aroma type spearmint (Application example 20) | 0.25 | 0.25 |
| Sum | 100.0 | 100.0 |

Application Example 24: Toothpaste with Spearmint Aroma

| | |
|---|---|
| Deionized water | 36.39 |
| Glycerin | 20 |
| Solbrol M (Sodium salt) | 0.15 |
| Sodium monofluorphosphate | 0.76 |
| Saccharin | 0.2 |
| Dicalciumphosphate-Dihydrate | 36 |
| Aerosil ® 200 (Silica) | 3 |
| Sodium carboxymethylcellulose | 1.2 |
| Sodium laurylsulfate (Texapon) | 1.3 |
| Aroma type spearmint (Application example 20) | 1 |

Application Example 25: Candy

| | | |
|---|---|---|
| Water | 2.75 | 2.5 |
| Sugar | Q.S. | Q.S. |
| Glucose syrup | 36.9 | 36 |
| Maltose | — | 2 |

-continued

|  |  |  |
|---|---|---|
| Palm kernel oil | — | 0.8 |
| Citric acid | — | 0.25 |
| Ginseng extract | — | 0.4 |
| Blue coloring | — | 0.01 |
| Aroma type spearmint (Application example 20) | 0.25 | 0.35 |
| Sum | 100.0 | 100.0 |

Application Example 26: Tomato Cream Soup

| Tomato powder | Q.S. |
|---|---|
| Sugar | 17 |
| Starch | 16.75 |
| Fat powder | 13 |
| Salt | 7 |
| Potato granulate | 5 |
| Milk protein | 2 |
| Yeast extract | 1 |
| Olive oil | 1 |
| Onion powder | 1 |
| Garlic powder | 0.5 |
| Dried parsley | 0.3 |
| Malic acid | 0.06 |
| Ginger extract | 0.15 |
| Basil aroma (spray-dried) | 0.08 |
| Spray-dried composition example 19a | 0.3 |
| Sum | 100 |

All ingredients are mixed. Subsequently, 120 g of this mixture are dissolved with 1000 ml of boiling water.

Application Example 27: Instant Tomato Soup

| Tomato powder | Q.S. |
|---|---|
| Sugar | 25 |
| Potato starch | 23.75 |
| Fat powder | 7.7 |
| Salt | 4.7 |
| Milk powder (26% Fat) | 3 |
| beetroot juice concentrate (spray-dried) | 1.22 |
| Citric acid (water-free) | 0.73 |
| Yeast extract | 0.73 |
| Carotin (10%) powder | 0.04 |
| Vitamin B2/Riboflavin powder | 0.01 |
| Basil aroma (spray-dried) | 0.01 |
| Spray-dried composition (example 19a) | 0.3 |
| Sum | 100 |

All ingredients are mixed and packed in portion bags of 24.5 g each. For the preparation, the content of one bag is emptied into a cup and dissolved with 230 ml of boiling water. Stirr well and wait a few minutes before consumption.

The invention claimed is:

1. A method for manufacturing a mixture comprising rotundone comprising:
   a) reacting wood oil(s), extract(s) and/or natural resin(s) containing guaiol and bulnesol with one or several organic acid(s),
   b) separating a guaiene containing fraction from a mixture obtained in a),
   c) oxidizing the separated guaiene containing fraction of b),
   d) optionally, heating an oxidized mixture obtained in c), and
   e) separating a rotundone containing fraction from the mixture obtained in c) or d), if present, to obtain a rotundone containing mixture.

2. A method according to claim 1, wherein the organic acid(s) used in a) is or are selected from the group consisting of citric acid, malic acid, tartaric acid, and oxalic acid.

3. A method according to claim 1, wherein in a) the weight ratio of wood oil(s), extract(s) and/or natural resin(s) containing guaiol and bulnesol to organic acid or organic acids is between 50:1 to 3:1.

4. A method according to claim 1, wherein the reaction in a) takes place in the presence of a co-solvent or several co-solvents.

5. A method according to claim 1, wherein a reaction temperature of the reaction in a) is between 160 and 260° C., and/or the reaction time of the reaction in a) is between 1 and 20 h, and/or the reaction in a) is conducted at normal pressure or at negative pressure.

6. A method according to claim 1, wherein the separation of the guaiene containing fraction from the mixture obtained or provided in a) takes place in b) by distillation.

7. A method according to claim 1, wherein the oxidation of the guaiene containing fraction of b) takes place in c) with ambient air and/or pure oxygen as oxidizing agent and/or at a temperature of 60 to 150° C., and/or with a gas amount of oxidizing agent from ≥10 to ≤1000l/h, per kg of precursor and/or over a period of time of 10 to 60 h.

8. A method according to claim 1, wherein a peroxide number of the mixture obtained in c) or d), if present, is <30 meq O/kg.

9. A method according to claim 1, wherein one or more entrainer(s) selected from the group consisting of triacetin and triethylcitrate in a weight ratio of mixture obtained in c) or d), if present, to entrainer(s) of 4:1 to 1:4, is or are added to the mixture in e) before and/or during distillation, and/or one or more co-solvent(s) selected from the group consisting of polyethylene glycols and palatinol Z, is or are added in a weight ratio of mixture obtained in c) or d), if present, to co-solvent(s) of 10:1 to 1:5.

10. A method according to claim 1, wherein the separation of the rotundone containing fraction from the mixture obtained in c) or d), if present, takes place in e) by distillation.

11. A rotundone containing mixture comprising rotundone, bulnesene, guaiene, guaiol and bulnesol as well as optionally triethylcitrate and/or triacetin, wherein the rotundone containing mixture is producible according to the method of claim 1.

12. A method for generating, imparting or modifying one or several taste and/or olfactory impression(s) comprising incorporating a rotundone containing mixture of claim 11 into a composition.

13. A preparation or intermediate good comprising a mixture according to claim 11.

14. A preparation or intermediate good according to claim 13, further comprising one or several (further) flavouring and/or odorous substance(s), wherein the total amount of the rotundone containing mixture is sufficient to modify one or several taste and/or olfactory impressions of the (further) flavouring and/or odorous substance(s).

15. A method for manufacturing a preparation or intermediate good according to claim 13 comprising:
   providing the rotundone containing mixture as well as one or several further components, wherein the further component or several further components is/are selected from the group consisting of flavouring and odorous substances, and
   mixing the rotundone containing mixture with the further component(s).

16. The method according to claim 1, wherein the wood oil(s), extract(s) and/or natural resin(s) of a) contain 15 to 45% by weight guaiol and 25 to 55% by weight bulnesol.

17. The method according to claim 1 comprising d) heating the oxidized mixture obtain in c) for 1 to 3 hours at 110 to 150° C.

18. The method according to claim 6, wherein the wherein the separation of the guaiene containing fraction from the mixture obtained or provided in a) takes place in b) by distillation at 1.0 to 20.0 mbar and a sump temperature of 90 to 175° C.

19. A method according to claim 7, wherein the oxidation of the guaiene containing fraction of b) takes place in c) with ambient air and/or pure oxygen as oxidizing agent at a temperature of 60 to 150° C. with a gas amount of oxidizing agent from ≥10 to ≤1000 l/h, per kg of precursor over a period of time of 10 to 60 h.

20. A method according to claim 8, wherein the peroxide number of the mixture obtained in c) or d), if present, is <20 meq O/kg.

\* \* \* \* \*